United States Patent

Zierke et al.

Patent Number: 5,196,433
Date of Patent: Mar. 23, 1993

[54] 3-SUBSTITUTED PYRIDINEMETHANOLS AND FUNGICIDES CONTAINING THEM

[75] Inventors: Thomas Zierke, Boehl-Inggelheim; Eberhard Ammermann, Heppenheim; Gisela Lorenz, Neustadt, all of Fed. Rep. of Germany

[73] Assignee: BASF Aktiengesellschaft, Ludwigshafen, Fed. Rep. of Germany

[21] Appl. No.: 893,844

[22] Filed: Jun. 4, 1992

[30] Foreign Application Priority Data

Jun. 26, 1991 [DE] Fed. Rep. of Germany ....... 4121049

[51] Int. Cl.⁵ .................. A01N 43/40; C07D 213/30
[52] U.S. Cl. .................... 514/277; 514/357; 546/329; 546/330; 546/339; 546/343; 546/344
[58] Field of Search ............... 514/277, 357; 546/344, 546/343, 329, 330, 339

[56] References Cited

U.S. PATENT DOCUMENTS

| | | | |
|---|---|---|---|
| 3,396,224 | 8/1968 | Van Heyningen | 514/277 |
| 4,699,652 | 10/1987 | Zehnder | 71/94 |
| 5,112,828 | 5/1992 | Zipperer et al. | |

FOREIGN PATENT DOCUMENTS 0435127 7/1991 European Pat. Off.

*Primary Examiner*—C. Warren Ivy
*Assistant Examiner*—A. A. Owens
*Attorney, Agent, or Firm*—Oblon, Spivak, McClelland, Maier & Neustadt

[57] ABSTRACT

Compounds of the Formula

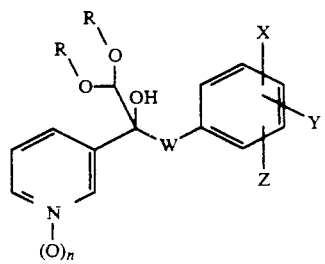

where
R is alkyl or cycloalkyl,
X,Y,Z are hydrogen, halogen, alkyl, alkoxy, alkoximino, haloalkyl, cyano, niro or substituted or unsubstituted phenyl or phenoxy,
W is a single bond or one of the groups —CH₂—, —CH(CH₃)— or —CH₂CH₂— and
n is 0 or 1, and
plant-tolerated acid addition salts thereof, and fungicides containing these compounds.

7 Claims, No Drawings

3-SUBSTITUTED PYRIDINEMETHANOLS AND FUNGICIDES CONTAINING THEM

The present invention relates to novel 3-substituted pyridinemethanols, the use thereof as fungicides, fungicidal compositions containing the novel active ingredients and methods of combating fungi with these active ingredients.

It is known to use 3-pyridinemethanols, e.g., α,α-bis-(4-chlorophenyl)-3-pyridinemethanol (disclosed in U.S. Pat. No. 3,396,224) and 4-(2,4-dichlorophenyl)-3-(3-pyridyl)-2-butanone ethylene ketal (disclosed in EP-A-209,854), as fungicides. EP-A-435,127 teaches pyridinyldioxolanes, e.g., 2-(4-fluorobenzyl)-4-(pyridin-3-yl)-5-(2,4-dichlorophenyl)-1,3-dioxolane, as fungicides. However, their fungicidal action is not always completely satisfactory. The object was therefore to provide novel 3-pyridinemethanols having a different chemical structure and a good fungicidal action.

We have now found novel 3-pyridylethanediols of the formula 1

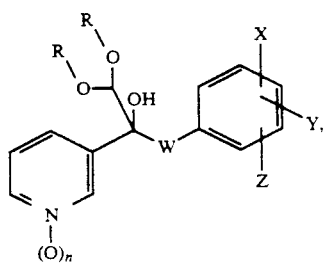

where
- R is straight-chain or branched $C_1$–$C_6$-alkyl or $C_3$–$C_6$-cycloalkyl,
- X,Y,Z are identical or different and each is hydrogen, halogen, $C_1$–$C_4$-alkyl, $C_1$–$C_4$-alkoxy, $C_1$–$C_4$-alkoximino, haloalkyl, cyano, nitro or unsubstituted or halo-substituted phenyl or phenoxy,
- W is a single bond or one of the groups —$CH_2$—, —$CH(CH_3)$— or —$CH_2CH_2$— and
- n is 0 or 1, and plant-tolerated acid addition salts thereof. The novel compounds have a surprisingly good fungicidal action which is better than that of prior art fungicides.

R may denote $C_1$–$C_4$-alkyl, especially methyl, ethyl, n-propyl, isopropyl, n-butyl, but-2-yl, isobutyl, tert.-butyl, n-pentyl, pent-2-yl, pent-3-yl, neopentyl, 3-methylbut-2-yl, n-hexyl, hex-2-yl, hex-3-yl, 2-methylpent-1-yl, 3-methylpent-1-yl, 4-methylpent-1-yl, 2-ethylbut-1-yl, 3-ethylbut-1-yl, cyclopropyl, cyclobutyl, cyclopentyl and cyclohexyl.

As a result of the substituents X, Y and Z and the phenyl ring, the invention embraces mono- to tri-substituted phenyl rings, e.g., phenyl, biphenyl, biphen-2-yl, biphen-3-yl, biphen-4-yl, halophenyl, 4-chlorophenyl, 4-fluorophenyl, 4-bromophenyl, 2-chlorophenyl, 2-fluorophenyl, 2-bromophenyl, 2,4-dichlorophenyl, 2-bromo-4-chlorophenyl, 2-chloro-4-bromophenyl, 2-chloro-4-fluorophenyl, 2,3-dichlorophenyl, 2-chloro-3-fluorophenyl, 2-fluoro-4-chlorophenyl, 2-chloro-3-fluoro-4-chlorophenyl, 2-bromo-4-fluorophenyl, 2-bromo-3-fluoro-4-chlorophenyl, 2,6-dichlorophenyl, halo-$C_1$–$C_4$-alkylphenyl, 2-trifluoromethylphenyl, 3-trifluoromethylphenyl, 4-trifluoromethylphenyl, 2-chloro-4-trifluoromethylphenyl, 2-chloro-3-trifluoromethylphenyl, 2,3-dichloro-4-trifluoromethylphenyl, 2-chloro-4-phenylphenyl, $C_1$–$C_4$-alkylphenyl, 2-methylphenyl, 4-methylphenyl, 4-tert.-butylphenyl, 2-chloro-4-methylphenyl, 2-methyl-4-chlorophenyl, 2,4-dimethylphenyl, 2,3-dimethylphenyl, $C_1$–$C_4$-alkoxyphenyl, 2-methoxyphenyl, 4-methoxyphenyl, 2-chloro-4-methoxyphenyl, 2-methyl-4-methoxyphenyl, 4-tert.-butoxyphenyl, $C_1$–$C_4$-alkoximinophenyl, 4-methoximinophenyl, 4-ethoximinophenyl, 2-chlor-4-methoximinophenyl, 4-cyanophenyl, 2-chloro-4-cyanophenyl, 2-cyano-4-chlorophenyl, 2-cyanophenyl, 2-nitrophenyl, 4-nitrophenyl, 2-chloro-4-nitrophenyl, 4-phenoxyphenyl and 4-(4'-chlorophenoxy)-phenyl.

Examples of plant-tolerated salts are acid addition salts with inorganic mineral acids, such as hydrochlorides, hydrobromides, sulfates, phosphates and nitrates, salts with formic acid or with alkylcarboxylic acids, such as acetates, 2-ethylhexanoates and oxalates, and salts with arylsulfonic acids, such as benzenesulfonates, toluenesulfonates and dodecylbenzenesulfonates.

The novel compounds of the formula 1 generally contain centers of asymmetry. They are usually obtained in the form of racemates or diastereomer mixtures. The pure diastereomers can be isolated from some of the novel compounds by distillation, column chromatography or on the basis of solubility differences. Pure enantiomers may be obtained for example by splitting the racemate with chiral auxiliary reagents by known methods, or via diastereomer salts. For the use of the novel compounds as fungicides, both the diastereomers and the enantiomers, and the stereoisomer mixtures obtained in the synthesis are suitable. They are all encompassed by the invention.

compounds of the formula 1 in which n is 1 are obtained from the corresponding compounds of the formula 1 in which n is 0 by treating them with a peracid or with mixtures of acids, such as acetic acid and hydrogen peroxide.

The manufacturing methods for compounds of the formula 1 in which n is 0 may be illustrated by the following equations:

Equation 1:

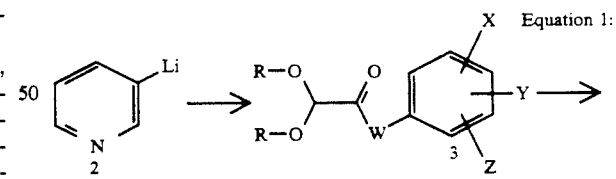

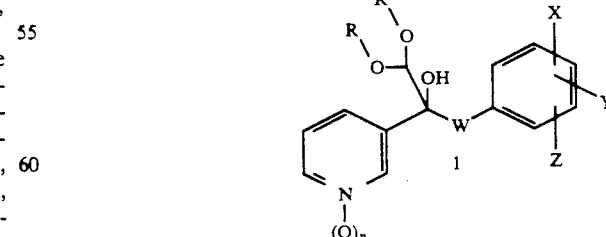

Equation 2:

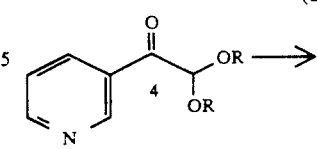

-continued

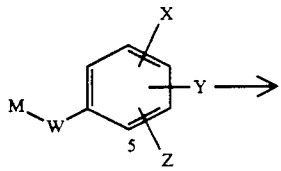

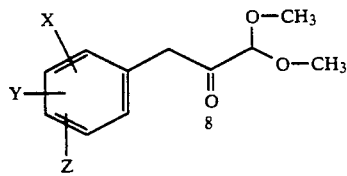

Compound 6 is known (K. Schrank, Chem. Ber. 100, pp. 2292-5, 1967). It is, as described in the literature (Baldwin et al., J. Med. Chem., 22, 692 1979), a starting material for compound 4 when R is $CH_3$. The preparation of 3-pyridyllithium 2 is as described in the literature (W. E. Parham et al., JOC 42, 1977, p. 275 et seq.).

The following examples describe the preparation of the novel compounds:

EXAMPLE 1

Preparation of 1,1-dimethoxy-2-hydroxy-2-(3-pyridyl)-3-(2,4-dichlorophenyl)-propane (Example 4 in the table)

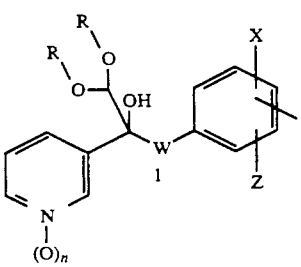

In formulae 2, 4 and 5 W, X, Y, Z and R have the same meanings as in formula 1. M in formula 5 stands, for instance, for lithium or the radicals MgCl or MgBr. Reactions with organometallic agents, such as shown in Equations 1 and 2, are reactions generally known in organic chemistry (cf, for instance, Organikum, 15. ed. 1977, p. 623 et seq.). Advantageously, such a reaction is carried out by metering the ketone component at from $-50°$ to $+50°$ C. into a mixture of from 1 to 2 equivalents of the organometallic compound in an inert solvent, preferably diethyl ether, methyl tert-butyl ether, tetrahydrofuran or a mixture thereof. Ketones of the formula 3 are generall known compounds, but some of them are novel. They may be prepared by a variety of known methods, such as described for example in EP-A-222 217 or DE-A-40 26 788. A method which is also preferred is illustrated by Equation 3 ($R=CH_3$, $W=CH_2$ and $M=MgCl$): Equation 3:

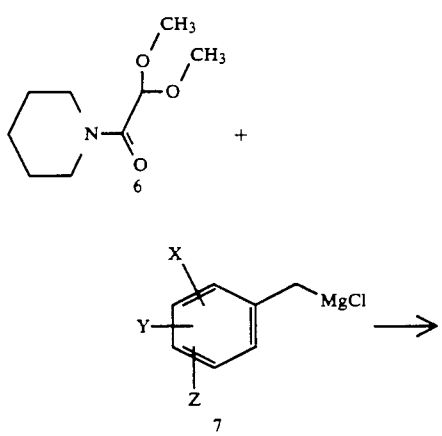

At $-70°$ C., 88.9 g (0.337 mol) of 1,1-dimethoxy-3-(2,4-dichlorophenyl)propan-2-one in 100 ml of diethyl ether ($Et_2O$) is dripped into a solution of 0.371 mol of 3-pyridyllithium in 1.1 liters of $Et_2O$ prepared from n-butyllithium and 3-bromopyridine. After half an hour at $-70°$ C., the solution is slowly heated up to 0° C. Isopropanol and then water is added, and the reaction solution is extracted with 1N hydrochloric acid. The acidic aqueous phase is then neutralized with $NaHCO_3$ and extracted with methylene chloride ($CH_2Cl_2$). After drying over $Na_2SO_4$, all the volatile constituents are removed in a rotary evaporator. A yellowish red oil is obtained. Yield: 56.1 g (48.7%).

$^1$H-NMR ($CDCl_3/TMS_{int}$): $\delta$/ppm = 3.08 (s,broad,1H), 3.33 (d,1H), 3.48 (d,1H), 3.53 (s,6H), 4.35 (s,1H), 6.98 (d,2H), 7.20 (dd,1H), 7.28 (d,1H), 7.75 (m,1H), 8.5 (dd,1H), 8.73 (d,1H)

Preparation of the starting material 1,1-dimethoxy-3-(2,4-dichlorophenyl)-propan-2-one A solution of 95 g (0.5 mol) of dimethoxyacetyl piperidide in 200 ml of tetrahydrofuran (THF) is dripped into a solution of 2,4-dichlorobenzylmagnesium chloride in 300 ml of diethyl ether ($Et_2O$) prepared from 13.2 g (0.55 mol) of magnesium shavings and 76.8 g (0.55 mol) of 2,4-dichlorobenzyl chloride. After the mixture has been kept for 2 hours at room temperature (20° C.) and for 2 hours at 50° C. it is worked up by adding 250 ml of cold 20% strength $NH_4Cl$ solution. The aqueous phase is extracted twice with $Et_2O$. The combined organic phases are dried over $Na_2SO_4$, filtered and evaporated down. A yellow oil is obtained. Yield: 73 g (56%).

$^1$H-NMR ($CDCl_3/TMS_{int}$): $\delta$/ppm = 3.48 (s,6H), 4.0 (s,2H), 4.55 (s,1H), 3.2 (d,1H), 3.4 (d,1H), 7.08-7.4 (m,3H)

The following compounds of the general formula 1 according to the invention (n=0) may be prepared analogously:

TABLE

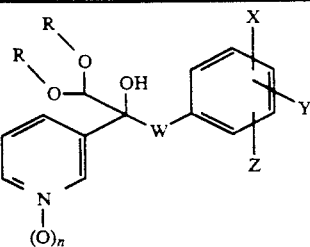

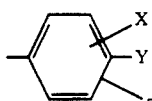

| No. | W | R | | Physical data |
|---|---|---|---|---|
| 1 | — | Methyl | 4-Fluorophenyl | mp.: 105–110° C. |
| 2 | —CH$_2$— | Methyl | Phenyl | oil, NMR: 3.5(s, 6H) |
| 3 | —CH$_2$— | Methyl | 2,4-Dimethylphenyl | oil, NMR: 2.1(s, 3H), 2.23(s, 3H), 3.5(s, 3H) |
| 4 | —CH$_2$— | Methyl | 2,4-Dichlorophenyl | oil, NMR: 3.53(s, 6H) |
| 5 | —CH$_2$— | Methyl | 4-Chlorophenyl | oil, NMR: 3.2(d, 2H), 3.5(s, 6H), 4.3(s, 1H) |
| 6 | — | Methyl | Phenyl | oil, NMR: 3.38(s, 3H), 3.4(s, 3H), 4.7(s, 1H) |
| 7 | — | Methyl | 2,4-Dichlorophenyl | oil, NMR: 3.3(s, 3H), 3.6(s, 3H), 5.1(s, 1H) |
| 8 | — | Methyl | 4-Methylphenyl | oil, NMR: 2.33(s, 3H), 3.38(s, 3H), 3.42(s, 3H), 4.7(s, 1H) |
| 9 | — | Methyl | 4-Methoxyphenyl | oil, NMR: 3.38(s, 3H), 3.42(s, 3H), 3.8(s, 3H), 4.65(s, 1H) |
| 10 | — | Methyl | Biphen-4-yl | oil, NMR: 3.4(s, 3H), 3.42(s, 3H), 4.7(s, 1H) |
| 11 | —CH$_2$— | Methyl | 2-Chlorophenyl | oil, NMR: 3.35(d, 1H), 3.52(s, 6H), 3.56(d, 1H), 4.4(s, 1H) |
| 12 | —CH$_2$— | Methyl | 3,4-Dichlorophenyl | oil, NMR: 3.13(d, 1H), 3.2(d, 1H), 3.50(s, 3H), 3.52(s, 3H), 4.3(s, 1H) |
| 13 | —CH$_2$— | Methyl | 3-Trifluorophenyl | mp.: 94–103° C. |
| 14 | — | Methyl | 4-Chlorophenyl | oil, NMR: 3.4(s, 6H), 4.6(s, 1H) |
| 15 | —CH$_2$— | Methyl | 4-Fluorophenyl | oil, NMR: 3.2(dd, 2H), 3.5(s, 6H), 4.32(s, 1H) |
| 16 | —CH$_2$— | Methyl | 2-Chloro-6-fluorophenyl | mp.: 63–65° C. |
| 17 | — | Ethyl | 4-Fluorophenyl | |
| 18 | —CH$_2$— | Ethyl | Phenyl | |
| 19 | —CH$_2$— | Ethyl | 2,4-Dimethylphenyl | |
| 20 | —CH$_2$— | Ethyl | 2,4-Dichlorophenyl | |
| 21 | —CH$_2$— | Ethyl | 4-Chlorophenyl | |
| 22 | — | Ethyl | Phenyl | |
| 23 | — | Ethyl | 2,4-Dichlorophenyl | |
| 24 | — | Ethyl | 4-Methylphenyl | |
| 25 | — | Ethyl | 4-Methoxyphenyl | |
| 26 | — | Ethyl | Biphen-4-yl | |
| 27 | —CH$_2$— | Ethyl | 2-Chlorophenyl | |
| 28 | —CH$_2$— | Ethyl | 3,4-Dichlorophenyl | |
| 29 | —CH$_2$— | Ethyl | 3-Trifluorophenyl | |
| 30 | — | Ethyl | 4-Chlorophenyl | |
| 31 | —CH$_2$— | Ethyl | 4-Fluorophenyl | |
| 32 | —CH$_2$— | Ethyl | 2-Chloro-6-fluorophenyl | |
| 33 | — | n-Propyl | 4-Fluorophenyl | |
| 34 | —CH$_2$— | n-Propyl | Phenyl | |
| 35 | —CH$_2$— | n-Propyl | 2,4-Dimethylphenyl | |
| 36 | —CH$_2$— | n-Propyl | 2,4-Dichlorophenyl | |
| 37 | —CH$_2$— | n-Propyl | 4-Chlorophenyl | |
| 38 | — | n-Propyl | Phenyl | |
| 39 | — | n-Propyl | 2,4-Dichlorophenyl | |
| 40 | — | n-Propyl | 4-Methylphenyl | |
| 41 | — | n-Propyl | 4-Methoxyphenyl | |
| 42 | — | n-Propyl | Biphen-4-yl | |
| 43 | —CH$_2$— | n-Propyl | 2-Chlorophenyl | |
| 44 | —CH$_2$— | n-Propyl | 3,4-Dichlorophenyl | |
| 45 | —CH$_2$— | n-Propyl | 3-Trifluorophenyl | |
| 46 | — | n-Propyl | 4-Chlorophenyl | |
| 47 | —CH$_2$— | n-Propyl | 4-Fluorophenyl | |
| 48 | —CH$_2$— | n-Propyl | 2-Chloro-6-fluorophenyl | |
| 49 | — | n-Butyl | 4-Fluorophenyl | |
| 50 | —CH$_2$— | n-Butyl | Phenyl | |
| 51 | —CH$_2$— | n-Butyl | 2,4-Dimethylphenyl | |
| 52 | —CH$_2$— | n-Butyl | 2,4-Dichlorophenyl | |
| 53 | —CH$_2$— | n-Butyl | 4-Chlorophenyl | |
| 54 | — | n-Butyl | Phenyl | |
| 55 | — | n-Butyl | 2,4-Dichlorophenyl | |
| 56 | — | n-Butyl | 4-Methylphenyl | |
| 57 | — | n-Butyl | 4-Methoxyphenyl | |
| 58 | — | n-Butyl | Biphen-4-yl | |
| 59 | —CH$_2$— | n-Butyl | 2-Chlorophenyl | |
| 60 | —CH$_2$— | n-Butyl | 3,4-Dichlorophenyl | |
| 61 | —CH$_2$— | n-Butyl | 3-Trifluorophenyl | |
| 62 | — | n-Butyl | 4-Chlorophenyl | |
| 63 | —CH$_2$— | n-Butyl | 4-Fluorophenyl | |
| 64 | —CH$_2$— | n-Butyl | 2-Chloro-6-fluorophenyl | |

TABLE-continued

[Structural formula showing a compound with R-O, R-O, OH, W substituents connected to a pyridine N(O)n ring, and an X,Y,Z-substituted phenyl ring]

[Phenyl ring with X, Y, Z substituents]

| No. | W | R | X,Y,Z-phenyl | Physical data |
|---|---|---|---|---|
| 65 | —CH₂— | iso-Propyl | 2,4-Dichlorophenyl | |
| 66 | —CH₂— | Methyl | 2-Fluoro-4-chlorophenyl | |
| 67 | —CH₂— | Methyl | 4-Fluoro-2-chlorophenyl | |
| 68 | —CH₂— | c-Hexyl | 2,4-Dichlorophenyl | |
| 69 | —CH₂— | Ethyl | 2-Fluoro-4-chlorophenyl | |
| 70 | —CH₂— | Ethyl | 4-Fluoro-2-chlorophenyl | |

Compounds of the formula 1 in which n is 1 may be prepared from the compounds in the table by treating them with a peracid such as metachloroperbenzoic acid or peracetic acid, and then separating off the carboxylic acid which was formed by washing with NaHCO₃ solution.

The novel compounds of the formula 1 are suitable as fungicides.

The fungicidal compounds I according to the invention, or agents containing them, may be applied for instance in the form of directly sprayable solutions, powders, suspensions (including high-percentage aqueous, oily or other suspensions), dispersions, emulsions, oil dispersions, dusting, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

Normally, the plants are sprayed or dusted with the active ingredients, or the seeds of the plants are treated with the active ingredients.

The formulations are produced in known manner, for example by extending the active ingredient with solvents and/or carriers, with or without the use of emulsifiers and dispersants; if water is used as diluent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as ligninsulfite waste liquors and methylcellulose.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylpheol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene a'kyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

Examples of formulations are given below:

I. A solution of 90 parts by weight of compound no. 1 and 10 parts by weight of N-methyl-α-pyrrolidone, which is suitable for application in the form of very fine drops.

II. A mixture of 20 parts by weight of compound no. 2, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in water, a dispersion is obtained.

III. An aqueous dispersion of 20 parts by weight of compound no. 3, 40 parts by weight of cyclohexanone, 30 parts by weight of isobutanol, 20 parts by weight of the adduct of 40 moles of ethylene oxide and 1 mole of castor oil.

IV. An aqueous dispersion of 20 parts by weight of compound no. 4, 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. A hammer-milled mixture of 80 parts by weight of compound no. 5, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in water, a spray liquor is obtained.

VI. An intimate mixture of 3 parts by weight of compound no. 6 and 97 parts by weight of particulate kaolin. The dust contains 3 wt % of the active ingredient.

VII. An intimate mixture of 30 parts by weight of compound no. 7, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 8, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 9, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate and 68 parts by weight of a paraffinic mineral oil.

The novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The compounds are applied by treating the fungi or the seeds, plants or materials to be protected against fungus attack, or the soil, with a fungicidally effective amount of the active ingredients.

The active ingredients may be applied before or after infection of the materials, plants or seed by the fungi.

The novel compounds I are particularly useful for controlling the following plant diseases:

*Erysiphe graminis* in cereals,
*Erysiphe cichoracearum* and *Sphaerotheca fuliginea* in cucurbits,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
*Phytophthora infestans* in potatoes and tomatoes,
Fusarium and Verticillium species in various plants,
*Plasmopara viticola* in grapes,
Alternaria species in fruit and vegetables.

The novel compounds may also be used for protecting materials (timber), e.g., against Paecilomyces variotii.

The fungicidal agents generally contain from 0.1 to 95, and preferably from 0.5 to 90, % by weight of active ingredient.

Depending on the type of effect desired, the application rates are from 0.02 to 3 kg of active ingredient per hectare.

When the active ingredients are used for treating seed, the application rates are generally from 0.001 to 50, and preferably from 0.01 to 10, g per kg of seed.

When used as fungicides, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole, 2-thiocyanatomethylthiobenzothiazole,
1,4-dichloro-2,5-dimethoxybenzene,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

USE EXAMPLES

The prior art active ingredient 2-(4-fluorobenzyl)-4-(pyridin-3-yl)-5-(2,4-dichlorophenyl)-1,3-dioxolane (A) disclosed in EP 435,127 was used for comparison purposes.

USE EXAMPLE 1

Action on Botrytis cinerea in paprika

Paprika seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus Botrytis cinerea, and placed at 22° to 24° C. in a chamber of high humidity. After 5 days, the disease had spread to such a great extent on the untreated plants that the necroses covered the major portion of the leaves.

The results show that active ingredients 3, 4, 5, 10, 11, 12 and 13, when applied as spray liquors containing 500 ppm of active ingredient, have a better fungicidal action (10% leaf attack) than prior art active ingredient A (70% leaf attack).

USE EXAMPLE 2

Action on Pyrenophora teres

Barley seedlings of the "Igri" variety were sprayed to runoff at the 2-leaf stage with aqueous suspensions containing (dry basis) 80% of active ingredient and 20% emulsifier. After 24 hours the plants were inoculated with a spore suspension of the fungus Pyrenophora teres and placed for 48 hours in a high-humidity climatic cabinet kept at 18° C. The plants were then cultivated for a further 5 days in the greenhouse at 20°-22° C. and a relative humidity of 70%. The extent of fungus spread was then determined.

The results show that active ingredients 3, 4 and 5, when applied as spray liquors containing 500 ppm of active ingredient, have a better fungicidal action (10% leaf attack) than prior art active ingredient A (50% leaf attack).

We claim:

1. A compound of the formula 1

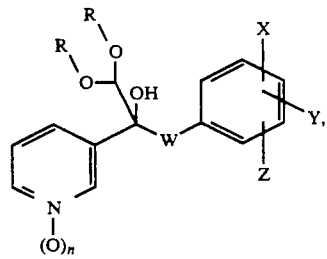

where
R is $C_1-C_6$-alkyl or $C_3-C_6$-cycloalkyl,
X,Y,Z are identical or different and each is hydrogen, halogen, $C_1-C_4$-alkyl, $C_1-C_4$-alkoxy, $C_1-C_4$-alkoximino, haloalkyl, cyano, nitro or unsubstituted or halo-substituted phenyl or phenoxy,
W is a single bond or one of the groups —$CH_2$—, —$CH(CH_3)$— or —$CH_2CH_2$— and
n is 0 or 1, and
plant-tolerated acid addition salts thereof.

2. A fungicidal composition containing a solid or liquid carrier and a fungicidally effective amount of a compound of the formula 1

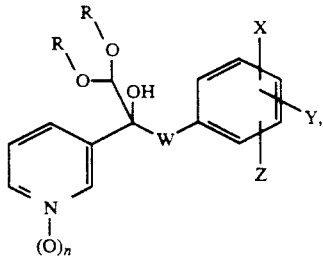

where

R is $C_1$-$C_6$-alkyl or $C_3$-$C_6$-cycloalkyl,

X,Y,Z are identical or different and each is hydrogen, halogen, $C_1$-$C_4$-alkyl, $C_1$-$C_4$-alkoxy, $C_1$-$C_4$-alkoximino, haloalkyl, cyano, nitro or unsubstituted or halo-substituted phenyl or phenoxy, W is a single bond or one of the groups —CH$_2$—, —CH(CH$_3$)— or —CH$_2$CH$_2$— and n is 0 or 1, or a plant-tolerated acid addition salt thereof.

3. A process for combating fungi, wherein a fungicidally effective amount of a compound of the formula 1

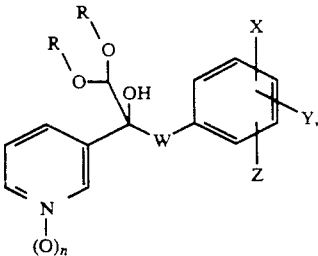

where

R is $C_1$-$C_6$-alkyl or $C_3$-$C_6$-cycloalkyl,

X,Y,Z are identical or different and each is hydrogen, halogen, $C_1$-$C_4$-alkyl, $C_1$-$C_4$-alkoxy, $C_1$-$C_4$-alkoximino, haloalkyl, cyano, nitro or unsubstituted or halo-substituted phenyl or phenoxy, W is a single bond or one of the groups —CH$_2$—, —CH(CH$_3$)— or —CH$_2$CH$_2$— and n is 0 or 1, or a plant-tolerated acid addition salt thereof, is allowed to act on the fungi, the plants, seeds or materials threatened by fungus attack, or the soil.

4. A compound of the formula 1 as set forth in claim 1, where W is a single bond, R is methyl and X and Y are H and Z is 4-fluoro.

5. A compound of the formula 1 as set forth in claim 1, where W is —CH$_2$—, R is methyl and X, Y, and Z are H.

6. A compound of the formula 1 as set forth in claim 1, where W is —CH$_2$—, R is methyl and X is H, Y is 2-methyl and Z is 4-methyl.

7. A compound of the formula 1 as set forth in claim 1, where W is —CH$_2$—, R is methyl and X is H, Y is 2-chloro and Z is 4-chloro.

* * * * *